US006929642B2

(12) United States Patent
Xiao et al.

(10) Patent No.: US 6,929,642 B2
(45) Date of Patent: Aug. 16, 2005

(54) RF DEVICE FOR TREATING THE UTERUS

(75) Inventors: Jia Hua Xiao, Bridgewater, NJ (US); Thomas P. Ryan, Flemington, NJ (US); Roddi J. Simpson, Jersey City, NJ (US); Alexander J. Sinton, Doylestown, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/278,466

(22) Filed: Oct. 23, 2002

(65) Prior Publication Data

US 2004/0002703 A1 Jan. 1, 2004

Related U.S. Application Data

(63) Continuation-in-part of application No. 10/186,259, filed on Jun. 28, 2002, now abandoned.

(51) Int. Cl.[7] .............................................. A61B 18/18
(52) U.S. Cl. ....................................... 606/41; 128/898
(58) Field of Search ...................... 606/27–52; 128/898

(56) References Cited

U.S. PATENT DOCUMENTS

| | | | |
|---|---|---|---|
| 4,932,421 A | * | 6/1990 | Kaali et al. .................. 128/831 |
| 5,277,201 A | * | 1/1994 | Stern ............................ 607/98 |
| 5,449,380 A | | 9/1995 | Chin |
| 5,558,672 A | * | 9/1996 | Edwards et al. ............... 606/41 |
| 5,575,788 A | | 11/1996 | Baker et al. |
| 5,702,438 A | | 12/1997 | Avitall |
| 5,769,880 A | | 6/1998 | Truckai et al. |
| 5,776,129 A | * | 7/1998 | Mersch ......................... 606/31 |
| 5,848,969 A | * | 12/1998 | Panescu et al. .............. 600/462 |
| 5,916,213 A | * | 6/1999 | Haissaguerre et al. ........ 606/41 |
| 6,068,629 A | * | 5/2000 | Haissaguerre et al. ........ 606/41 |
| 6,161,047 A | | 12/2000 | King et al. |
| 6,197,022 B1 | * | 3/2001 | Baker ........................... 606/33 |
| 6,270,495 B1 | * | 8/2001 | Palermo ........................ 606/41 |
| 6,306,129 B1 | | 10/2001 | Little et al. |
| 6,475,212 B2 | | 11/2002 | Dobak, III et al. |
| 6,547,784 B1 | | 4/2003 | Thompson et al. |
| 6,620,161 B2 | * | 9/2003 | Schulze et al. ............... 606/51 |
| 2003/0212389 A1 | | 11/2003 | Durgin et al. |

OTHER PUBLICATIONS

Taylor & Francis Ltd., M.V. Prior, et al., "Treatment of Menorrhagia by Radiofrequency Heating", Int. J. Hyperthermia, vol. 7, No. 2, pp. 213–220 (1991).
The C.V. Mosby Co., W. Droegemueller, et al., "Cryocoagulation of the Endometrium at the Uterine Cornua", Am. J. Obstet. and Gynecol., vol. 131, No. 1, pp. 1–9 (May 1978).
The American College of Obstetricians and Gynecologists, A. Singer, et al., "Preliminary Clinical Experience with a Thermal Balloon Endometrial Ablation Method to Treat Menorrhagia", Obstet. Gynecol., vol. 83, No. 5, Part 1, pp. 732–734.
Mosby–Year Book, Inc., M. Baggish, et al., "A Computer-Controlled, Continuously Circulating, Hot Irrigating System for Endometrial Ablation", Am. J. Obstet. Gynecol., vol. 173, No. 6, pp. 1842–1848 (Dec. 1995).
Pending U.S. Appl. No. 10/186,259, entitled "RF Device for Treating the Uterus", filed Jun. 28, 2002, Inventors: Jia Hua Xiao, Thomas Ryan and Alexander J. Sinton.
Pending U.S. Appl. No. 10/262,513, entitled "Deployable Cryosurgical Catheter", filed Sep. 30, 2002, Inventors: Jia Hua Xiao and Simon Cohn.

* cited by examiner

*Primary Examiner*—Roy D. Gibson
*Assistant Examiner*—Pete Vrettakos (57) ABSTRACT

An electrode instrument is provided and includes an electrode head and a pair of electrodes for emitting RF energy for use in thermal ablation therapy. The electrodes are movable between a collapsed configuration and deployed configuration. When collapsed, the electrodes are proximate to each other, and when deployed, the electrodes are spaced apart from each other. The electrode instrument includes linkage mechanisms that are used to maintain the electrodes in their deployed configuration.

27 Claims, 10 Drawing Sheets

RF DEVICE FOR TREATING THE UTERUS

CROSS-REFERENCE TO RELATED APPLICATION

This application is a continuation-in-part of commonly owned U.S. application Ser. No. 10/186,259, entitled, "RF Device For Treating The Uterus", filed Jun. 28, 2002 has abandoned.

FIELD OF THE INVENTION

The present invention relates to an RF (radio frequency) device for use in the performance of thermal ablation, and more particularly, to an RF device for ablation of endometrial cells and tissue within the uterus.

BACKGROUND OF THE INVENTION

Millions of women suffer from excessive menstrual bleeding (menorrhagia). A commonly used therapy to treat menorrhagia involves ablating the endometrial lining that is responsible for the bleeding. Such ablation has been shown to reduce the bleeding, and in some instances, to cease the menstrual bleeding.

Various methods have been used to ablate the endometrial lining of the uterus. One such method involves inserting a balloon catheter into the uterus, filling the balloon with a thermally conductive fluid, and then heating the fluid to thermally ablate the endometrial lining of the uterus. Although thermal balloon therapy is effective for treating menorrhagia in women who have a smooth uterine lining, such balloon therapy is not recommended for women who have uterine conditions such as myomas, polyps, or irregular uterine shapes.

Accordingly, there is a need for a therapy that involves the use of thermal ablation for treating menorrhagia in women who have benign uterine pathology and that is easy to use and to control.

SUMMARY OF THE INVENTION

In accordance with the present invention, an electrode instrument is provided and used for thermal ablation therapy. An electrode head is included, which has a first and second electrode for emitting RF energy. The electrodes are movable between a collapsed configuration, in which the electrodes are proximate to each other, and a deployed configuration, in which the electrodes are spaced apart from each other. A linkage mechanism is connected between the electrodes and is used to maintain the electrodes in their deployed configuration.

In accordance with one embodiment, the electrode instrument includes an effector strip for emitting RF energy. Tensioning means for varying the tension of the effector strip is also provided.

Other features and aspects of the present invention will become more fully apparent from the following detailed description of the exemplary embodiments, the appended claims and the accompanying drawings.

BRIEF DESCRIPTION OF THE DRAWINGS

For a more complete understanding of the present invention, reference is made to the following detailed description of the exemplary embodiments considered in conjunction with the accompanying drawings, in which.

DETAILED DESCRIPTION OF THE EXEMPLARY EMBODIMENT

Figure 1:
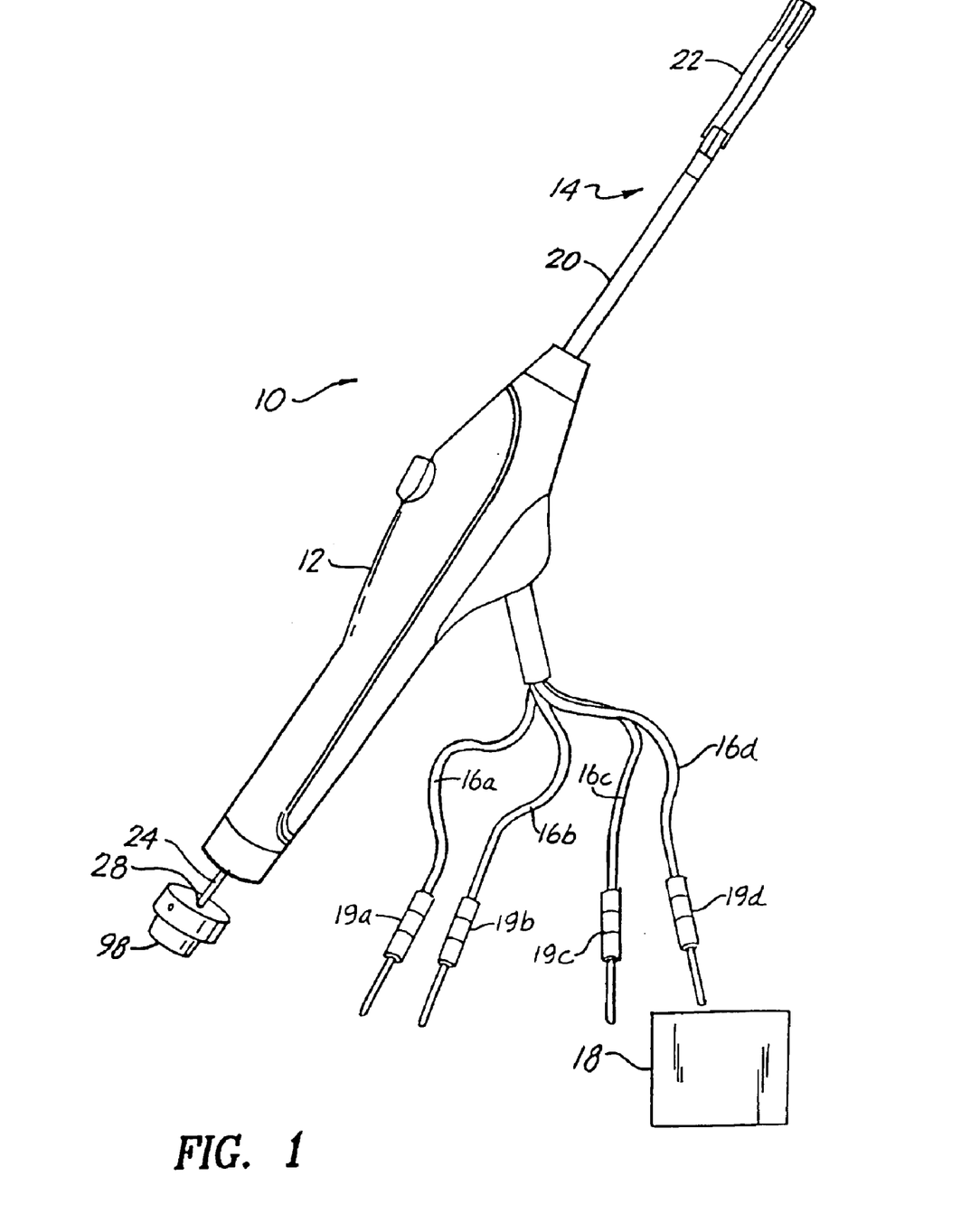
FIG. 1 is a front perspective view of an RF device constructed in accordance with the present invention.

FIG. 1 shows an RF device 10 having a handgrip portion 12 and an RF catheter 14 connected thereto. Various cables 16a–d are attached to the handgrip portion 12 and are provided for connecting the RF device 10 to an RF generator 18 (shown in phantom). The RF generator 18 is electrically connected to the RF catheter 14 and serves to provide bipolar RF energy, wherein the current flow is localized between an active and return electrode, to the RF device 10. Electrical leads 19a–d are electrically connected to the RF generator 18, via one of the cables 16a–d, respectively, and extend to the RF catheter 14. During use, the electrical leads 19a–d carry RF energy from the RF generator 18 to the RF catheter 14.

Figure 2:
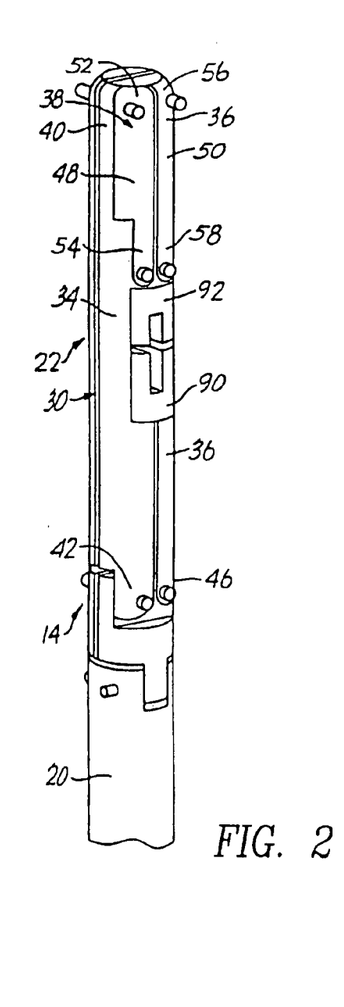
FIG. 2 is a front perspective view of an RF catheter of the RF device shown in FIG. 1, which shows an electrode head in a fully relaxed configuration.
Figure 3:
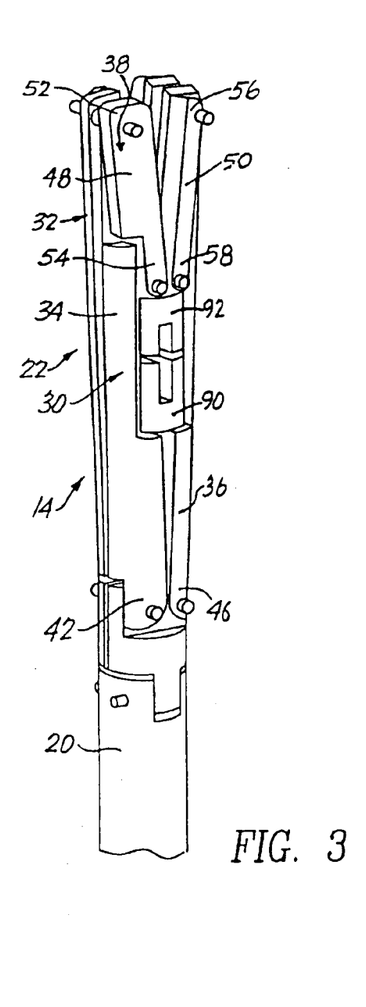
FIGS. 3 to 5 are sequential perspective views of the RF catheter, showing the progressive movement of the electrode head as it moves from the relaxed configuration to a deployed configuration.
Figure 4:
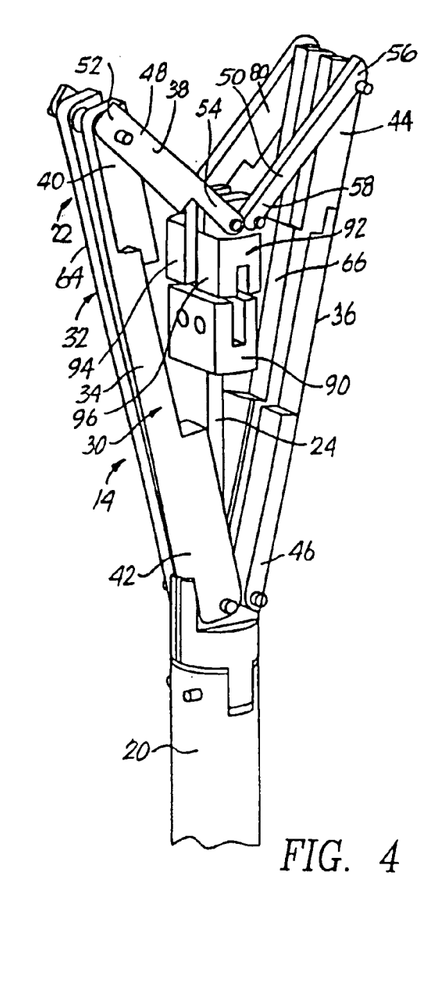
Figure 5:
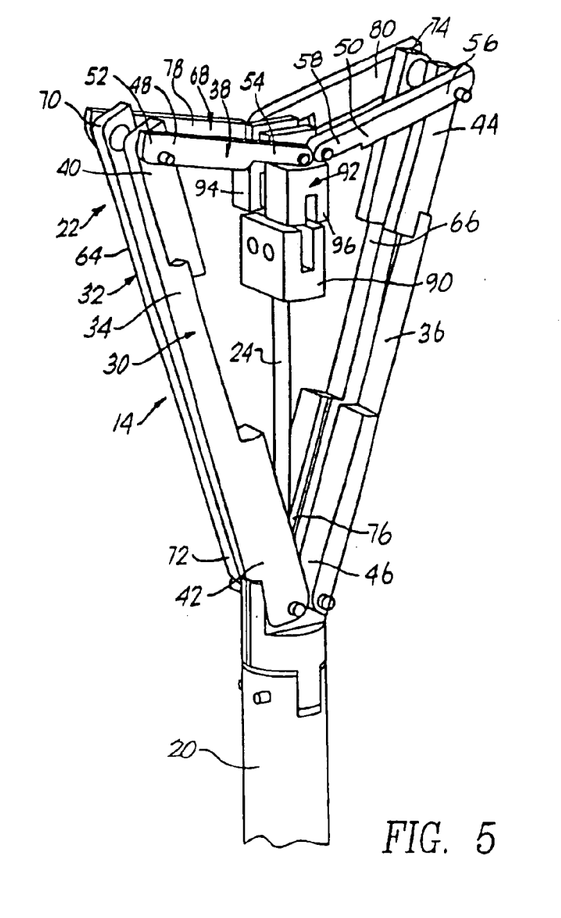
Figure 6:
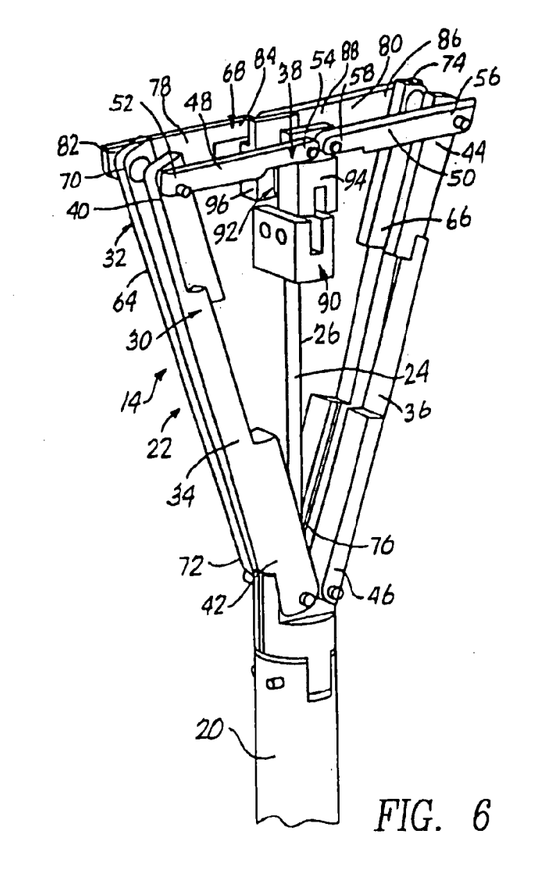
FIG. 6 is a view similar to the view shown in FIGS. 2 to 5, except that the electrode head is in the fully deployed configuration.

With reference to FIGS. 2 to 6, the RF catheter 14 includes an outer sheath 20 and an electrode head 22 attached thereto. For reasons to be discussed hereinafter, the electrode head 22 is sized and shaped to move between a deployed configuration as shown in FIG. 6, in which it is substantially triangularly-shaped so as to approximate the shape of the uterine cavity, and a relaxed configuration as shown in FIG. 2, in which it is substantially cylindrically-shaped so as to facilitate transcervical insertion into the uterine cavity.

Referring to FIG. 1, the RF device 10 includes an actuator rod 24 that extends between the proximal and distal ends thereof. The actuator rod 24 is sized and shaped to be received within the handgrip portion 12 and within the RF catheter 14. A distal end 26 (see FIG. 6) of the actuator rod 24 extends beyond the outer sheath 20 and into the electrode head 22. The actuator rod 24 also includes a proximal end 28 that extends beyond the handgrip portion 12.

With reference to FIGS. 2 to 6, the electrode head 22 includes a pair of RF applicators 30, 32 positioned adjacent to each other. As shown in FIG. 6, the RF applicator 30 has a pair of electrode members, one member includes an electrode leg 34 and an arm 48, and the other member includes an electrode leg 36 and an arm 50, for delivering RF energy. The polarity of the electrode members can be regulated such that the electrode leg 34 and the arm 48, the electrode leg 36 and the arm 50 can be activated as an active or return electrode. The electrode leg 34 has a distal end 40 and a proximal end 42, and likewise, the electrode leg 36 has a distal end 44 and a proximal end 46. Still referring to FIG. 6, the arm 48 is electrically isolated from the arm 50, and mechanically connected to the arm 50. The arm 48 has a distal end 52 and a proximal end 54, and the arm 50 has a distal end 56 and a proximal end 58 mechanically connected, but electrically isolated, to the proximal end 54 of the arm 48. More particularly, the distal end 52 of the arm 48 is connected to the distal end 40 of the electrode leg 34 and can pivot thereabout, while the distal end 56 of the arm 50 is connected to the distal end 44 of the electrode leg 36 and can pivot thereabout. The electrode leg 34 and the arm 48 are electrically connected to each other and to the cable 16a. Also, the electrode leg 36 and the arm 50 are electrically connected to each other and to the cable 16b.

The RF applicator 30 is sized and shaped to move between a closed configuration (see FIG. 2), in which the electrode legs 34, 36 are in a collapsed configuration, and an open configuration (see FIG. 6), in which the electrode legs 34, 36 are in a deployed configuration. With reference to FIG. 2, when the RF applicator 30 is in its closed configuration, the distal ends 40, 44 of the electrode legs 34, 36 are adjacent to each other, the proximal ends 42, 46 of the electrode legs 34, 36 are adjacent to each other, the distal ends 52, 56 of the arms 48, 50 are adjacent to each other, and the proximal ends 54, 58 of the arms 48, 50 are also adjacent to each other. Referring to FIG. 6, when the RF applicator 30 is in its open configuration, the distal ends 40, 44 of the electrode legs 34, 36 are spaced apart from each other so as to form a V-shaped figure, the distal ends 52, 56 of the arms 48, 50 are spaced apart from each other, and the proximal ends 54, 58 of the arms 48, 50 are adjacent to each other in a substantially linear fashion. In this manner, the arms 48, 50 collectively serve as a link 38 connected between the electrode legs 34, 36 for maintaining the electrode legs 34, 36 in their deployed configuration.

As shown in FIG. 6, the RF applicator 32 has a pair of electrode members, one member includes an electrode leg 64 and an arm 78 and the other member includes an electrode leg 66 and an arm 80 for delivering RF energy. The polarity of the electrode members can be regulated such that the electrode leg 64 and the arm 78, the electrode leg 66 and the arm 80 can be activated as an active or return electrode. The electrode leg 64 has a distal end 70 and a proximal end 72, and likewise, the electrode leg 66 has a distal end 74 and a proximal end 76. Still referring to FIG. 6, the arm 78 is electrically isolated from the arm 80, and mechanically connected to the arm 80. The arm 78 has a distal end 82 and a proximal end 84, and the arm 80 has a distal end 86 and a proximal end 88 mechanically connected, but electrically isolated, to the proximal end 84 of the arm 78. More particularly, the distal end 82 of the arm 78 is connected to the distal end 70 of the electrode leg 64 and can pivot thereabout, while the distal end 86 of the arm 80 is connected to the distal end 74 of the electrode leg 66 and can pivot thereabout. The electrode leg 64 and the arm 78 are electrically connected to each other and to the cable 16c. Also, the electrode leg 66 and the arm 80 are electrically connected to each other and to the cable 16d.

In a bipolar fashion, the electrode leg 34 and the arm 48 can be activated as the active electrode, while the electrode leg 36 and the arm 50 can be activated as the return electrode. The electrical connections can be switched such that the electrode leg 34 and the arm 48 can be activated as the active electrode, while the electrode leg 64 and the arm 78 can be activated as the return electrode. Other electrical connections can also be switched such that the electrode leg 64 and the arm 78 can be activated as the active electrode, while the electrode leg 66 and the arm 80 can be activated as the return electrode. Further, the electrical connections can be altered such that the electrode leg 36 and the arm 50 can be activated as the active electrode, while the electrode leg 66 and the arm 80 can be activated as the return electrode. The polarity can be regulated such that any other combination of electrode legs and arms can be activated as an active electrode and as a return electrode. The polarity can then be altered at various time intervals so as to facilitate thermal coverage of the uterine cavity. Because the electrode legs 34, 36, 64, 66 and the arms 48, 50, 78, 80 can be connected in various bipolar arrangements and switches electrical connections at various time intervals, increased thermal coverage is achieved.

The RF applicator 32 is sized and shaped to move between a closed configuration (see FIG. 2), in which the electrode legs 64, 66 are in a collapsed configuration, and an open configuration (see FIG. 6), in which the electrode legs 64, 66 are in a deployed configuration. When the RF applicator 32 is in its closed configuration, the distal ends 70, 74 of the electrode legs 64, 66 are adjacent to each other, the proximal ends 72, 76 of the electrode legs 64, 66 are adjacent to each other, the distal ends 82, 86 of the arms 78, 80 are adjacent to each other, and the proximal ends 84, 88 of the arms 78, 80 are also adjacent to each other. Referring to FIG. 6, when the RF applicator 32 is in its open configuration, the distal ends 70, 74 of the electrode legs 64, 66 are spaced apart from each other so as to form a V-shaped figure, the distal ends 82, 86 of the arms 78, 80 are spaced apart from each other, and the proximal ends 84, 88 of the arms 78, 80 are adjacent to each other in a substantially linear fashion. In this manner, the arms 78, 80 collectively serve as a link 68 connected between the electrode legs 64, 66 for maintaining the electrode legs 64, 66 in their deployed configuration.

Still referring to FIG. 6, a first piston 90 is attached to the distal end 26 of the actuator rod 24, while a second piston 92 is attached to the first piston 90 at one end and to the first and second links 38, 68 at an opposite end. More particularly, the second piston 92 has a first member 94 connected to the proximal ends 54, 58 of the arms 48, 50 and a second member 96 connected to the proximal ends 84, 88 of the arms 78, 80. The second piston 92 is sized and shaped to move between a first position (see FIG. 4), in which the first and second members 94, 96 are adjacent to each other such that the RF applicators 30, 32 are adjacent to each other, and a second position (see FIG. 6), in which the first and second members 94, 96 are spaced apart from each other such that the RF applicators 30, 32 move apart from each other.

As illustrated in FIGS. 2 to 6, the RF device 10 also includes a finger gripping flange 98 (see FIG. 1) connected to the proximal end 28 of the actuator rod 24, such that when the finger gripping flange 98 is pushed axially in a direction toward the electrode head 22, the actuator rod 24 slides the first and second pistons 90, 92 in a direction toward the first and second links 38, 68. As the first and second pistons 90, 92 slide toward the first and second links 38, 68, the RF applicators 30, 32 move from their closed configuration (see FIG. 2) to their open configuration (see FIG. 6). Also, as the first and second pistons 90, 92 slide toward the first and second links 38, 68, the second piston 92 moves from its first position to its second position (see FIG. 6). In the foregoing manner, the electrode head 22 is placed into its deployable configuration. When the finger gripping flange 98 is pulled axially in a direction away from the electrode head 22, the foregoing steps described above are reversed so as to place the electrode head 22 into its relaxed configuration.

Figure 7:
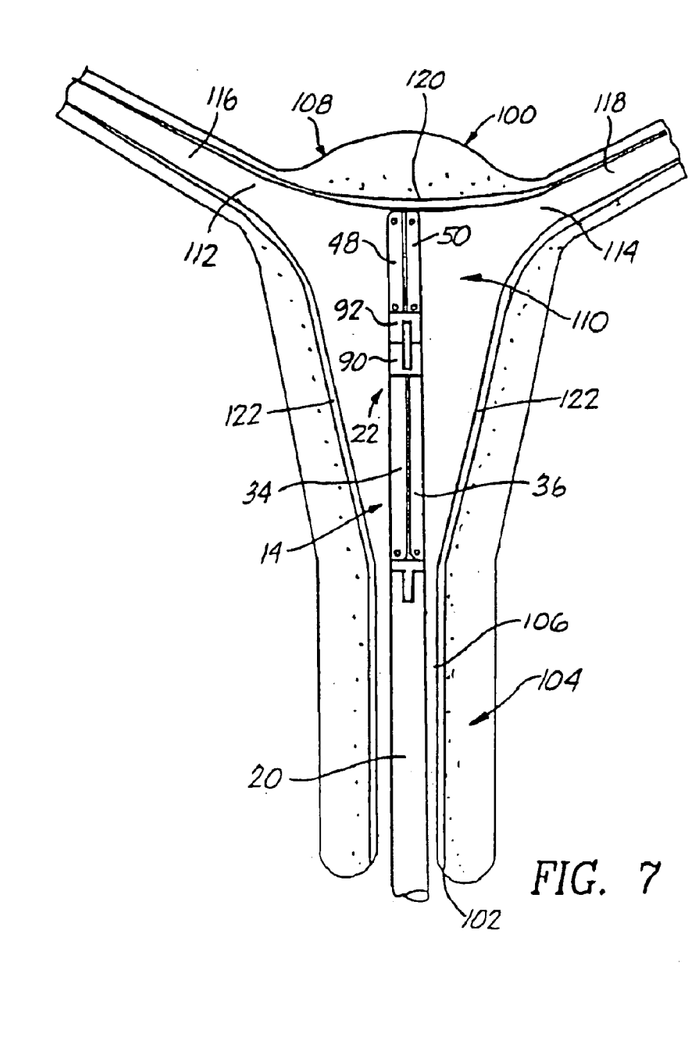
FIG. 7 is a schematic view of a female uterus and the RF device shown in FIG. 1, which shows a distal portion of the electrode head in contact with the uterine cavity.
Figure 8:
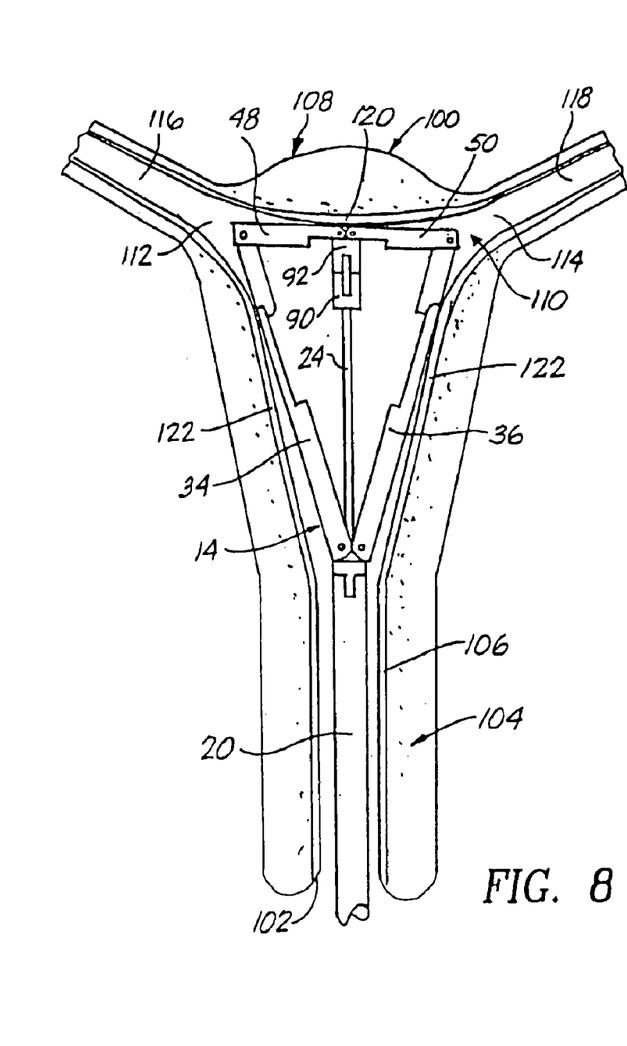
FIG. 8 is a view similar to the view shown in FIG. 7, except that the electrode head is in the deployed configuration.

In order to fully understand the advantages of the RF device 10, a brief overview of the female uterus 100 is discussed below with reference to FIGS. 7 and 8. The female uterus 100 includes an external cervical opening 102; a cervix 104 having a cervical canal 106; an uterus 108 having an uterine cavity 110; tubal ostia 112, 114; and Fallopian tubes 116, 118. The uterine cavity 110 is joined to the Fallopian tubes 116, 118 via their respective tubal ostia 112, 114. As illustrated in FIGS. 7 and 8, the uterine cavity 110 is substantially triangularly-shaped and includes a plurality of cavity walls in the form of a top wall (hereinafter referred to as a fundus 120) and side walls 122.

In operation, prior to inserting the electrode head 22 into the uterine cavity 110, the uterine sound (depth) is measured. More particularly, a sound (not shown) is inserted into the vaginal orifice (not shown) and guided through the cervical canal 106, and into the uterine cavity 110 until the sound is in contact with the fundus 120. The RF device 10 is then inserted transcervically into the vaginal orifice (not shown) until the electrode head 22 enters the cervix 104. Note that in the foregoing step, the electrode head 22 is in its fully relaxed configuration.

As illustrated in FIG. 7, the electrode head 22 is then guided in its relaxed configuration through the cervical canal 106, and into the uterine cavity 110 until the electrode head 22 is adjacent to the fundus 120 of the uterine cavity 110. Next, the electrode head 22 is deployed, in the manner described previously, into its fully deployed configuration as shown in FIG. 8, so as to contact the uterine cavity 110.

After the electrode head 22 is in its fully deployed configuration, voltage is supplied to the electrode legs 34, 36 of the RF applicator 30 and to the electrode legs 64, 66 of the RF applicator 32 such that RF energy is emitted therefrom to the tissues surrounding and between the electrode leg 34 and the arm 48, and the electrode leg 64 and the arm 78. RF energy is also emitted to the tissues surrounding and between the electrode leg 36 and the arm 50, and the electrode leg 66 and the arm 80 for a first predetermined time interval. The emitted RF energy heats and ablates these tissue areas. Then, the polarity of the electrode legs 34, 36 and of the electrode legs 64, 66 is altered such that one of the pair of electrode legs 34, 64 is activated as an active electrode and the other pair of electrode legs 36, 66 is activated as a return electrode. Voltage is supplied to the electrode legs 34, 36 of the RF applicator 30 and to the electrode legs 64, 66 of the RF applicator 32 such that RF energy is emitted therefrom to the tissues surrounding and between the electrode leg 34 and the arm 48, and the electrode leg 36 and the arm 50. RF energy is also emitted to the tissues surrounding and between the electrode leg 64 and the arm 78, and the electrode leg 66 and the arm 80 for a second predetermined time interval that is substantially equal to the first predetermined time interval. Alternatively, the first time interval does not approximate the second time interval. Then, the electrode head 22 is undeployed into its relaxed configuration. Lastly, the electrode head 22 is removed from the uterine cavity 110, the cervical canal 106, and the vaginal orifice (not shown).

Figure 9:
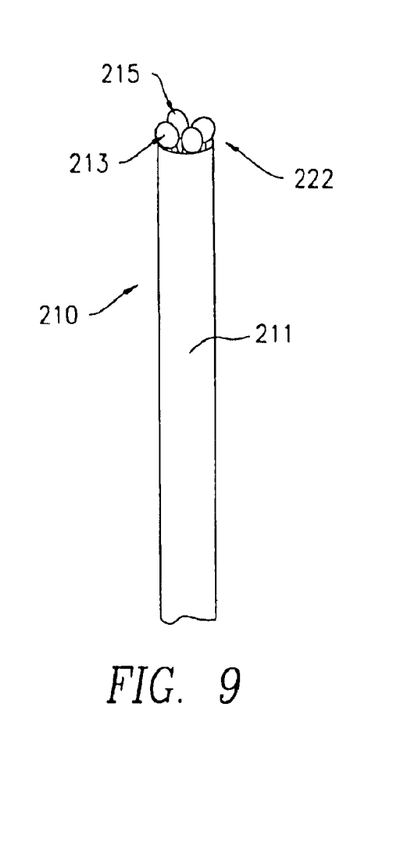
FIG. 9 is a front perspective view of an RF device in accordance with a second embodiment of the present invention, which shows a tube in a distal position.
Figure 10:
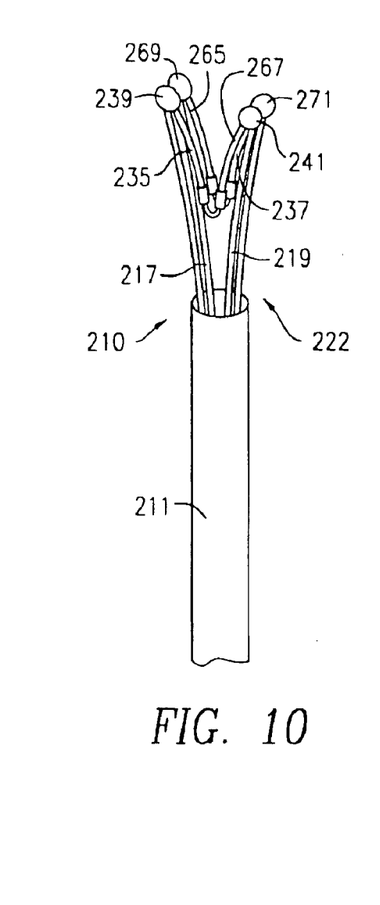
FIG. 10 is a sequential view of the RF device of FIG. 9, showing the tube between its distal and proximal positions.
Figure 11:
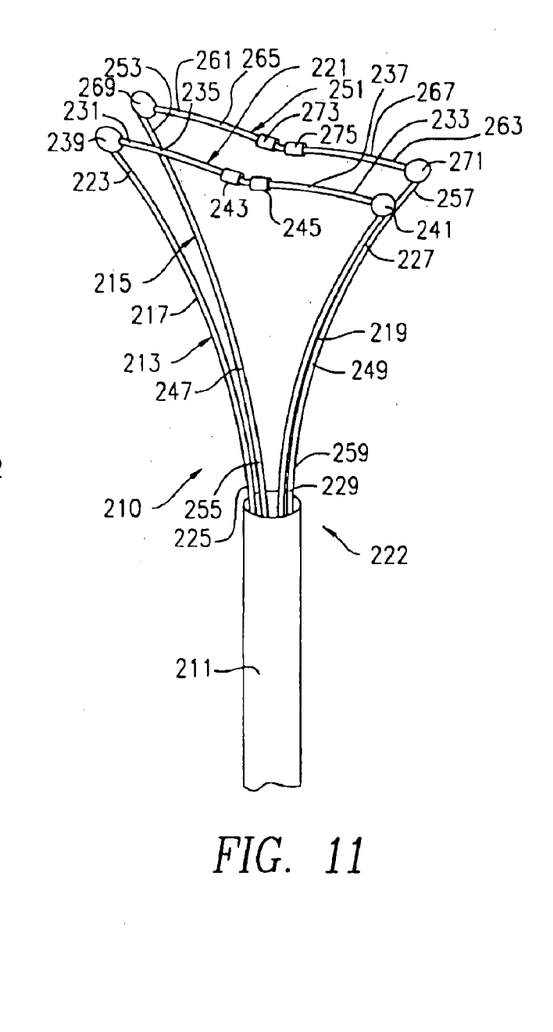
FIG. 11 is a view similar to the view shown in FIG. 9, except that the tube is in the proximal position, fully deployed.

A second exemplary embodiment of the present invention is illustrated in FIGS. 9 to 11. Elements illustrated in FIGS. 9 to 11 which correspond to the elements described above with reference to FIG. 1 have been designated by corresponding reference numerals increased by two hundred. In addition, elements illustrated in FIGS. 9 to 11 which do not correspond to the elements described above with reference to FIG. 1 have been designated by odd numbered reference numerals starting with reference number 211. The embodiment of FIGS. 9 to 11 operates in the same manner as the embodiment of FIG. 1, unless it is otherwise stated.

FIG. 9 shows an RF device 210 having a tube 211 which is linearly shaped and an electrode head 222 having a pair of spring wire electrodes 213, 215 for delivering RF energy. The spring wire electrodes 213, 215 are sized and shaped to be received within the tube 211. The tube 211 is slidable between a distal position in a direction toward the spring wire electrodes 213, 215 as shown in FIG. 9, in which the spring wire electrodes 213, 215 are substantially compressed within the tube 211 so as to facilitate transcervical insertion into the uterine cavity, and a proximal position in a direction away from the spring wire electrodes 213, 215 as shown in FIG. 11, in which the spring wire electrodes 213, 215 are released from the tube 211 and assume a substantially triangularly-shape so as to approximate the shape of the uterine cavity.

The spring wire electrodes 213, 215 are resilient and have a spring or shape memory such that when released, they assume their triangular shape. It is understood that the spring wire electrodes 213, 215 can be made from any spring or shape memory material.

With reference to FIG. 11, the spring wire electrode 213 is a continuous wire that forms a three-sided figure when released. More particularly, the spring wire electrode 213 forms a pair of members, one member includes an electrode leg 217 and an arm 235, and the other member includes an electrode leg 219 and an arm 237, for delivering RF energy. The electrode leg 217 has a distal end 223 and a proximal end 225, and likewise, the electrode leg 219 has a distal end 227 and a proximal end 229. The arms 235, 237 collectively serve as a central link 221 connected between the electrode legs 217, 219. Still referring to FIG. 11, the central link 221 includes a first end 231 connected to the distal end 223 of the electrode leg 217 and can pivot thereabout and a second end 233 connected to the distal end 227 of the electrode leg 219 and can pivot thereabout. The central link 221 is bendable such that when the tube 213 is in its distal position, the central link 221 bends so as to form the pair of substantially equal-sized arms 235, 237 (see FIG. 10), which facilitates insertion into the tube 213. The arm 235 is electrically isolated from the arm 237, and mechanically connected to the arm 237.

A first spherical ball 239 covers the distal end 223 of the electrode leg 217 and the first end 231 of the central link 221, while a second spherical ball 241 covers the distal end 227 of the electrode leg 219 and the second end 233 of the central link 221. The spherical ball 239 is used to electrically connect the electrode leg 217 to the arm 235. Likewise, the spherical ball 241 is used to electrically connect the electrode leg 219 to the arm 237. The balls 239, 241 are spherically shaped so as to provide a smooth surface for contact with the uterus. A pair of tabs 243, 245 is included and covers the central link 221. The tabs 243, 245 are used for electrical insulation and to mechanically connect the arm 235 to the arm 237.

With reference to FIG. 11, the spring wire electrode 215 is also a continuous wire that forms a three-sided figure when released. More particularly, the spring wire electrode 215 forms a pair of members, one member includes an electrode leg 247 and an arm 265 and the other member includes an electrode leg 249 and an arm 267. The electrode leg 247 has a distal end 253 and a proximal end 255, and likewise, the electrode leg 249 has a distal end 257 and a proximal end 259. The arms 265, 267 collectively serve as a central link 251 connected between the electrode legs 247, 249. Still referring to FIG. 11, the central link 251 has a third end 261 connected to the distal end 253 of the electrode leg 247 and can pivot thereabout and a fourth end 263 connected to the distal end 257 of the electrode leg 249 and can pivot thereabout. The central link 251 is bendable such that when the tube 243 is in its distal position, the central link 251 bends so as to form the pair of substantially equal-sized arms 265, 267 (see FIG. 10), which facilitates insertion into the tube 213. The arm 265 is electrically isolated from the arm 267, and mechanically connected to the arm 267.

A third spherical ball 269 covers the distal end 253 of the electrode leg 247 and the first end 261 of the central link 251, while a fourth spherical ball 271 covers the distal end 257 of the electrode leg 249 and the second end 263 of the central link 251. The spherical ball 269 is used to electrically connect the electrode leg 247 to the arm 265. Likewise, the spherical ball 271 is used to electrically connect the electrode leg 249 to the arm 267. The balls 269, 271 are spherically shaped so as to provide a smooth surface for contact with the uterus. A pair of tabs 273, 275 is included and covers the central link 251. The tabs 273, 275 are used for electrical insulation and to mechanically connect the arm 265 to the arm 267. The polarity can be regulated such that any combination of the electrode legs and the arms can be activated as an active electrode and as a return electrode.

A third exemplary embodiment of the present invention is illustrated in FIGS. 12 to 20. Elements illustrated in FIGS. 12 to 20 which correspond to the elements described above with reference to FIG. 1 have been designated by corresponding reference numerals increased by three hundred. In addition, elements illustrated in FIGS. 12 to 20 which do not correspond to the elements described above with reference to FIG. 1 have been designated by odd numbered reference numerals starting with reference number 311. The embodiment of FIGS. 12 to 20 operates in the same manner as the embodiment of FIG. 1, unless it is otherwise stated.

Figures 12, 13:
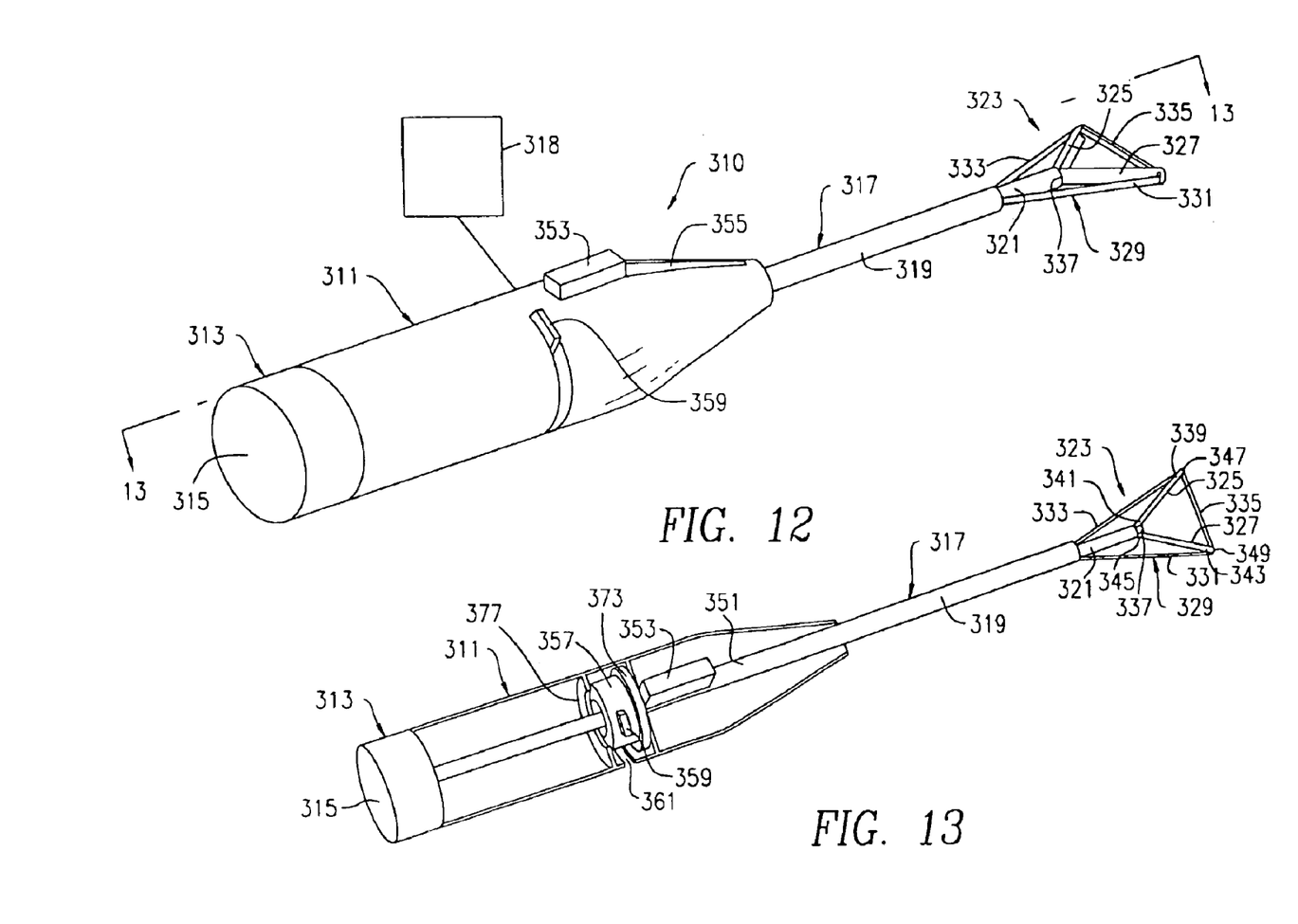
FIG. 12 is a front perspective view of an RF device in accordance with a third embodiment of the present invention.
FIG. 13 is a partial cross-sectional view of the RF device shown in FIG. 12, taken along section lines 13—13 and looking in the direction of the arrows, showing the interior of a handle portion.

FIG. 12 shows an RF device 310 having a handgrip portion 311 for providing means for manual manipulation and operation of the RF device 310 by a medical practitioner. The handgrip portion 311 includes a finger knob 313 for reasons to be described hereinafter at a proximal end 315 thereof. Still referring to FIG. 12, the RF device 310 includes an elongated sheath assembly 317 having an outer sheath 319 and an inner tube 321 coaxially received within the outer sheath 319. The RF device 310 further includes a linkage assembly 323 having a pair of jaws 325, 327 utilized to spread an effector strip 329 for emitting RF energy, as will be described in further detail hereinafter. The linkage assembly 323 and the effector strip 329 form the catheter head.

With reference to FIG. 12, an RF generator 318 (shown in phantom) is electrically connected to the effector strip 329 and utilized to provide either monopolar or bipolar RF energy to the RF device 310. The effector strip 329 is a patchwork of independent isolated electrically conductive patches, which include electrode legs 331, 333 (only a portion of which is shown in FIG. 12), and an arm 335, each of which can be activated as an active or return electrode. This allows the polarity of the effector strip 329 to be regulated such that any combination of conductive patches 331, 333, and 335 can be activated as an active electrode and as a return electrode. Each of the electrode legs 331, 333, and the arm 335 can contain multiple conductive patches, each of which can be activated as an active electrode and as a return electrode. The electrode legs 331, 333 and the arm 335 are flexible, allowing for improved conformity not only to the uterus interior but also to any pathology (e.g., small fibroids or polyps) and can wrap around the pathology's surface.

Figures 18, 19:
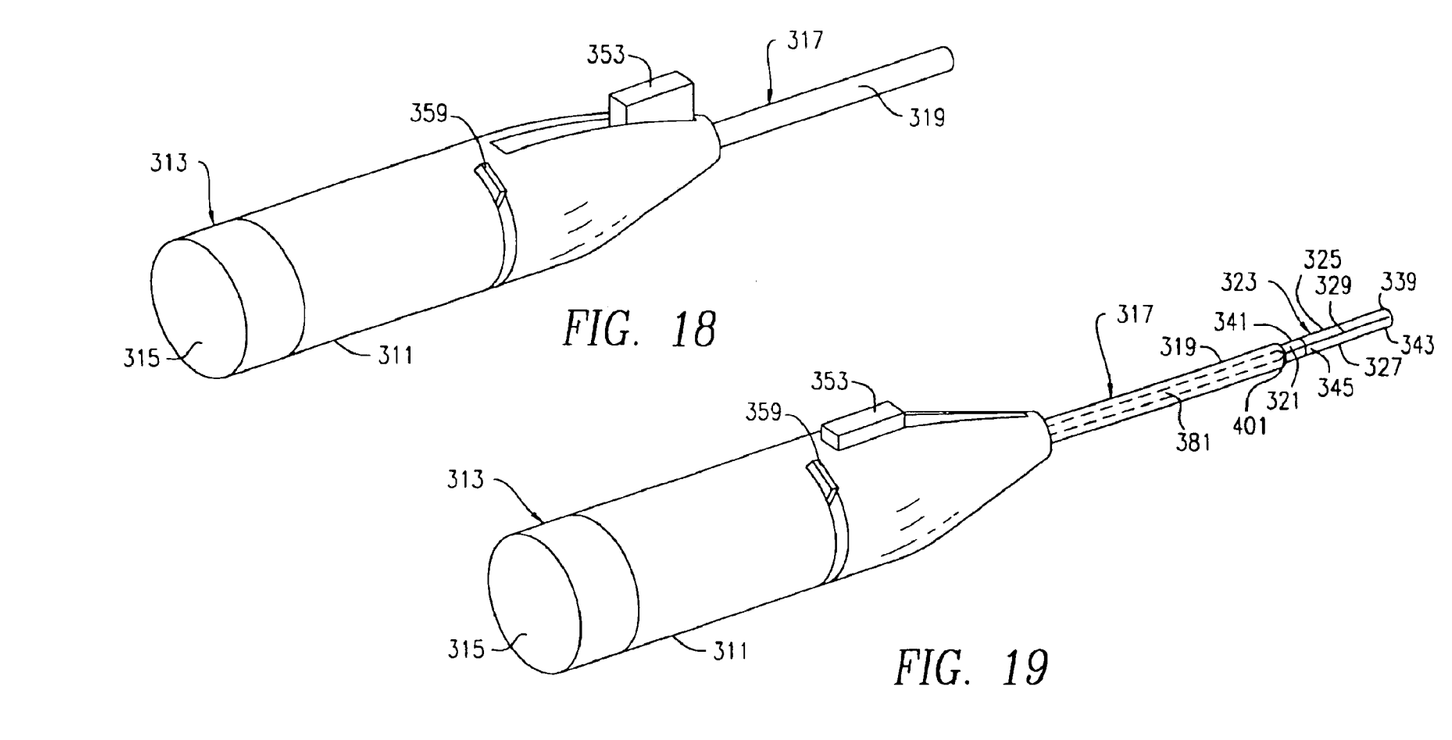
FIG. 18 is a front, perspective view of the RF device, which shows an outer sheath in its fully extended configuration.
FIG. 19 is a view similar to the view shown in FIG. 18, except that the outer sheath is in its retracted configuration.
Figure 20:
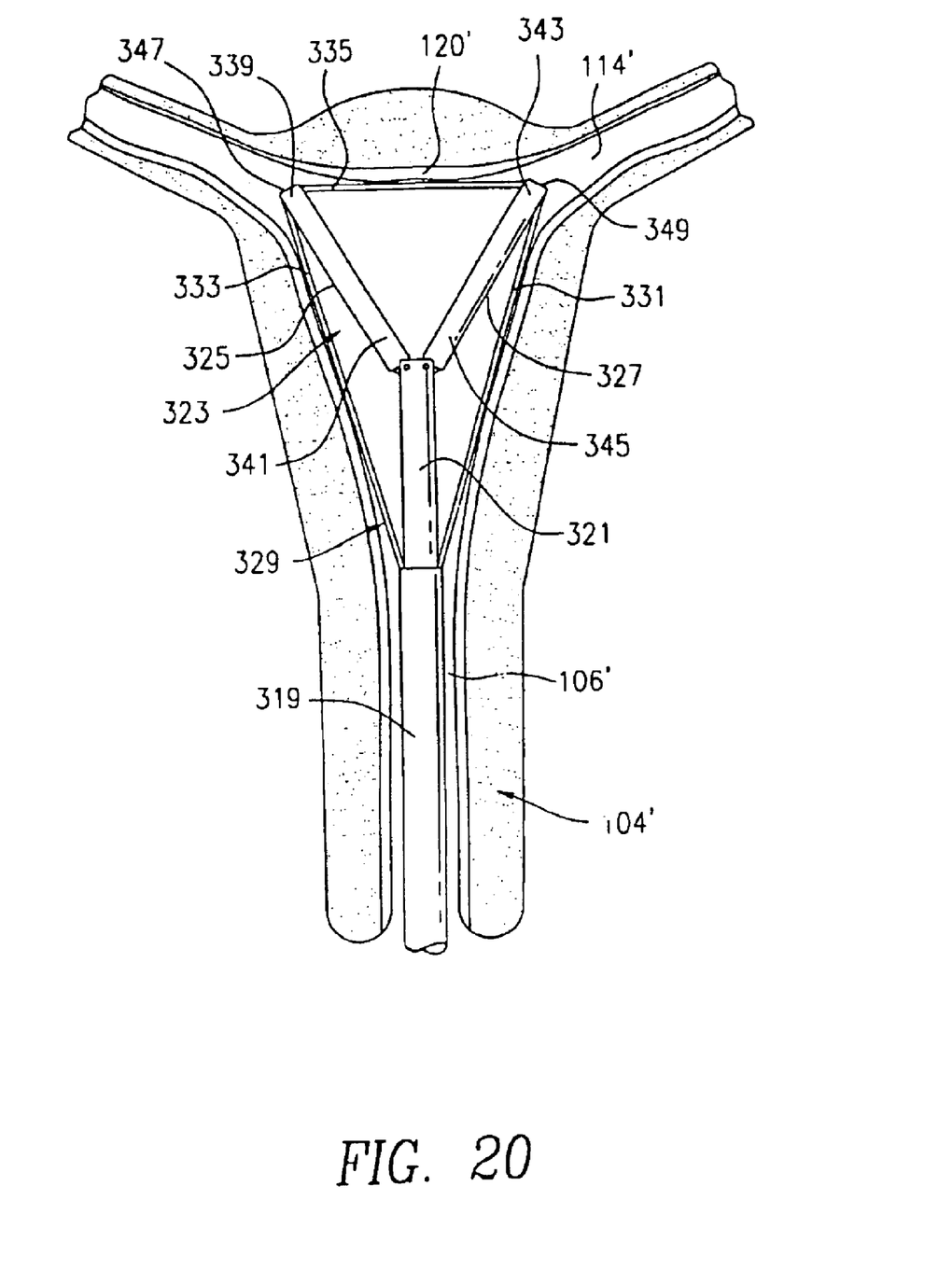
FIG. 20 is a schematic view of the female uterus and the RF device shown in FIG. 12, which shows a distal portion thereof in contact with the uterine cavity.

Referring to FIG. 13, the jaws 325, 327 are pivotally attached to the inner tube 321 at a distal end 337 thereof. The jaw 325 has a distal end 339 and a proximal end 341, and likewise, the jaw 327 has a distal end 343 and a proximal end 345. The jaws 325, 327 are sized and shaped to move between a closed configuration (see FIG. 19) and an open configuration (see FIG. 20). In the closed configuration, the linkage assembly 323 is substantially cylindrically-shaped so as to facilitate transcervical insertion into the uterine cavity. With reference to FIG. 19, when the jaws 325, 327 are in their closed configuration, the distal ends 339, 343 of the jaws 325, 327 are substantially proximate to each other and the proximal ends 341, 345 of the jaws 325, 327 are substantially proximate to each other. Referring to FIG. 20, when the jaws 325, 327 are in their open configuration, the distal ends 339, 343 of the jaws 325, 327 are spaced apart from each other so as to form a V-shaped figure while the proximal ends 341, 345 of the jaws 325, 327 remain substantially proximate to each other. The distal end 339 of the jaw 325 has a slot 347 sized and shaped to allow the effector strip 329 to pass therethrough, and likewise the distal end 343 of the jaw 327 has a slot 349 sized and shaped to allow the effector strip 329 to pass therethrough.

Referring to FIG. 19, when the jaws 325, 327 are in their closed configuration, the electrode legs 331, 333 (see FIG. 20) assume a collapsed configuration such that the electrode legs 331, 333 are substantially proximate to each other, and the arm 335 (see FIG. 20) bends so as to form a pair of substantially equal-sized segments (not shown), located between the jaws 325, 327. Alternatively, the arm 335 can extend along the longitudinal, exterior surface of the jaws 325, 327. With reference to FIG. 20, when the jaws 325, 327 are in their open configuration, the electrode legs 331, 333 assume a deployed configuration such that the electrode legs 331, 333 are remote from each other. The jaws 325, 327 of the linkage assembly 323 maintain the electrode legs 331, 333 in their deployed configuration. In the deployed configuration, the electrode legs 331, 331, and the arm 335 of the effector strip 329 cooperate to form a shape that approximates the shape of the uterine cavity.

As illustrated in FIG. 13, the sheath assembly 317 has a proximal end 351 inserted within the handgrip portion 311 and the distal end 337 which is sized and shaped to be insertable within the uterus for reasons discussed hereinafter. The sheath assembly 317 is linearly shaped.

Referring to FIGS. 12 and 13, the outer sheath 319 of the sheath assembly 317 is sized and shaped to move relative to the handgrip portion 311 and to the inner tube 321. More particularly, the outer sheath 319 includes an extension 353 that extends through a longitudinal slot 355 (see FIG. 12) in the handgrip portion 311. The extension 353 provides means for manual manipulation whereby it moves between a retracted position (see FIG. 19), in which the outer sheath 319 moves in a proximal direction toward the handgrip portion 311 such that the inner tube 321 and the effector strip 329 are partially exposed and the linkage assembly 323 is fully exposed, and an extended position (see FIG. 18), in which the outer sheath 319 moves in a distal direction away from the handgrip portion 311 such that the inner tube 321, the effector strip 329, and the linkage assembly 323 are covered by the outer sheath 319. When the outer sheath 319 is retracted, the jaws 325, 327 can move between their closed configuration (see FIG. 19) and their open configuration (see FIG. 20). The length of the effector strip 329 that is exposed is determined by the extent of retraction of the outer sheath 319. Accordingly, the amount of contact between the effector strip 329 and the uterine cavity can be regulated. The longitudinal slot 355 (see FIG. 12) is sized and shaped to allow the outer sheath 319 to move in an axial direction, and serves to prevent the outer sheath 319 from rotating.

With reference to FIG. 13, the handgrip portion 311 contains an outer cam 357 having a protrusion 359 that extends through a lateral slot 361 in the handgrip portion 311 and utilized to regulate the tension of the effector strip 329, as will be discussed in further detail hereinafter. The lateral slot 361 is sized and shaped to allow the outer cam 357 to rotate. A pair of lateral projections 377, 379 (see FIG. 17) is provided and serves to prevent the outer cam 357 from moving in an axial direction.

Figure 14:
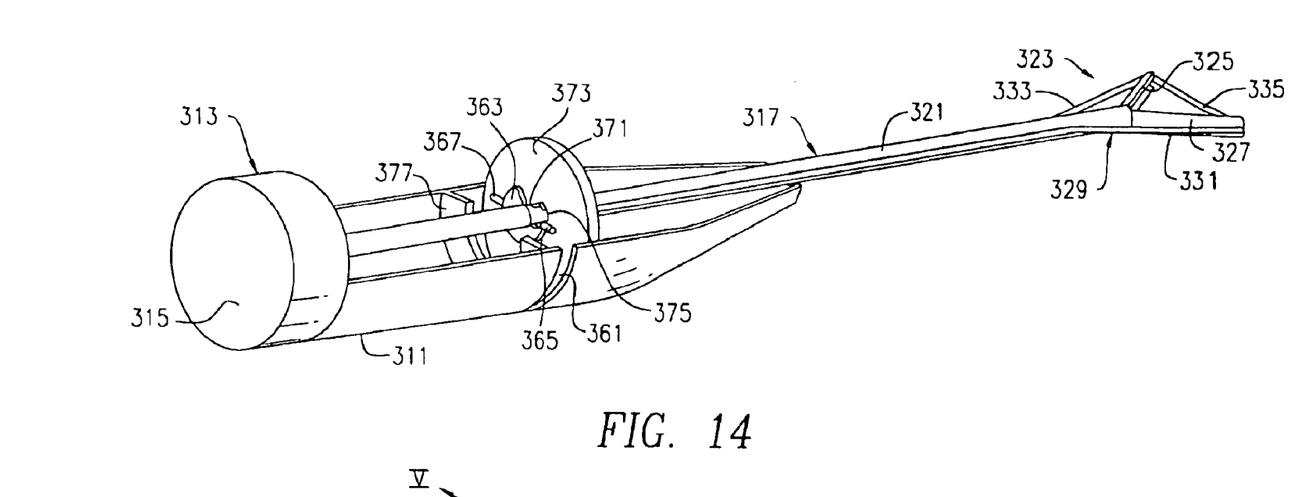
FIG. 14 is a partial cross-sectional view of the RF device shown in FIG. 13, showing an inner cam and an inner tube.
Figure 15:
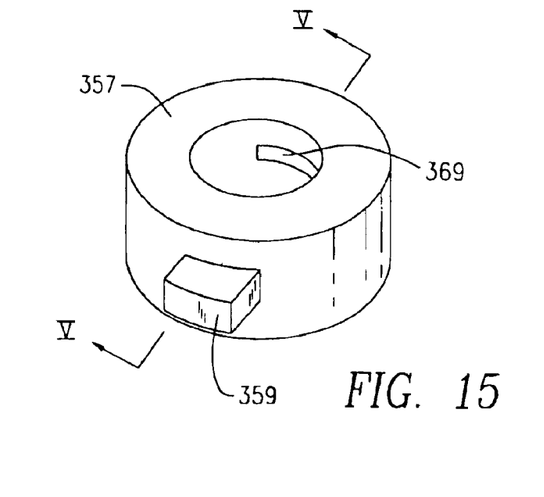
FIG. 15 is a perspective view of the outer cam.
Figure 16:
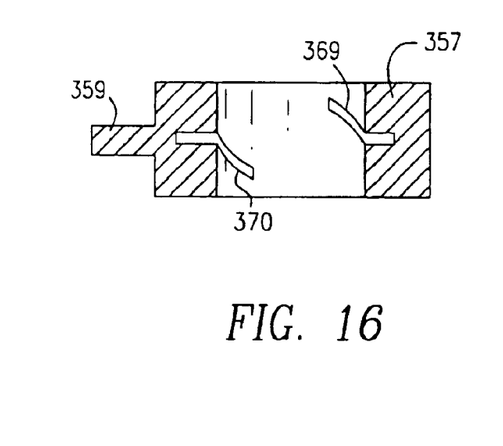
FIG. 16 is a cross-sectional view of the outer cam shown in FIG. 15, taken along section lines 16-16 and looking in the direction of the arrows.

Referring to FIGS. 13 and 14, the effector strip 329 is located between the outer sheath 319 and the inner tube 321 and extends along the longitudinal sides of the inner tube 321. Now referring to FIG. 14, an inner cam 363 is positioned between the outer cam 357 (see FIG. 13) and the inner tube 321. The inner cam 363 has a pair of cylindrical members 365, 367 extending therefrom. The cylindrical member 365 is received in a groove 369 (see FIGS. 15 and 16) provided in an interior section of the outer cam 357, and the cylindrical member 367 is received in a groove 370 (see FIG. 16) provided in the interior section of the outer cam 357. Referring to FIGS. 15 and 16, the groove 369 has a slanted, angled shape so as to cause the cylindrical member 365 to move in an axial direction. Likewise, the groove 370 has a slanted, angled shape so as to cause the cylindrical member 367 to move in an axial direction. As the outer cam 357 rotates, the groove 369 of the outer cam 357 cooperates with the cylindrical member 365 and the groove 370 cooperates with the cylindrical member 367 so as to move the inner cam 363 in an axial direction.

As illustrated in FIG. 14, the inner cam 363 serves to anchor a proximal end 371 of the effector strip 329 using conventional attaching means such as elastic. More particularly, as the inner cam 363 moves in an axial direction, the effector strip 329 moves concurrently therewith so as to alter the tension of the effector strip 329. By varying the tension of the effector strip 329, the contact between the effector strip 329 and the uterine cavity can be regulated so as to maximize the effectiveness of energy transfer and to facilitate the deployment and retraction of the jaws 325, 327 before or after surgery.

With further reference to FIG. 14, the proximal end of the inner tube 321 is sized and shaped to cooperate with the inner cam 363 and to allow axial movement of the inner cam 363. An anchoring disc 373 is attached to the inner tube 321 and to the handgrip portion 311 so as to lock the inner tube 321 in place relative to the handgrip portion 311. The anchoring disc 373 has openings 375 through which the effector strip 329 contacts the inner cam 363.

Figure 17:
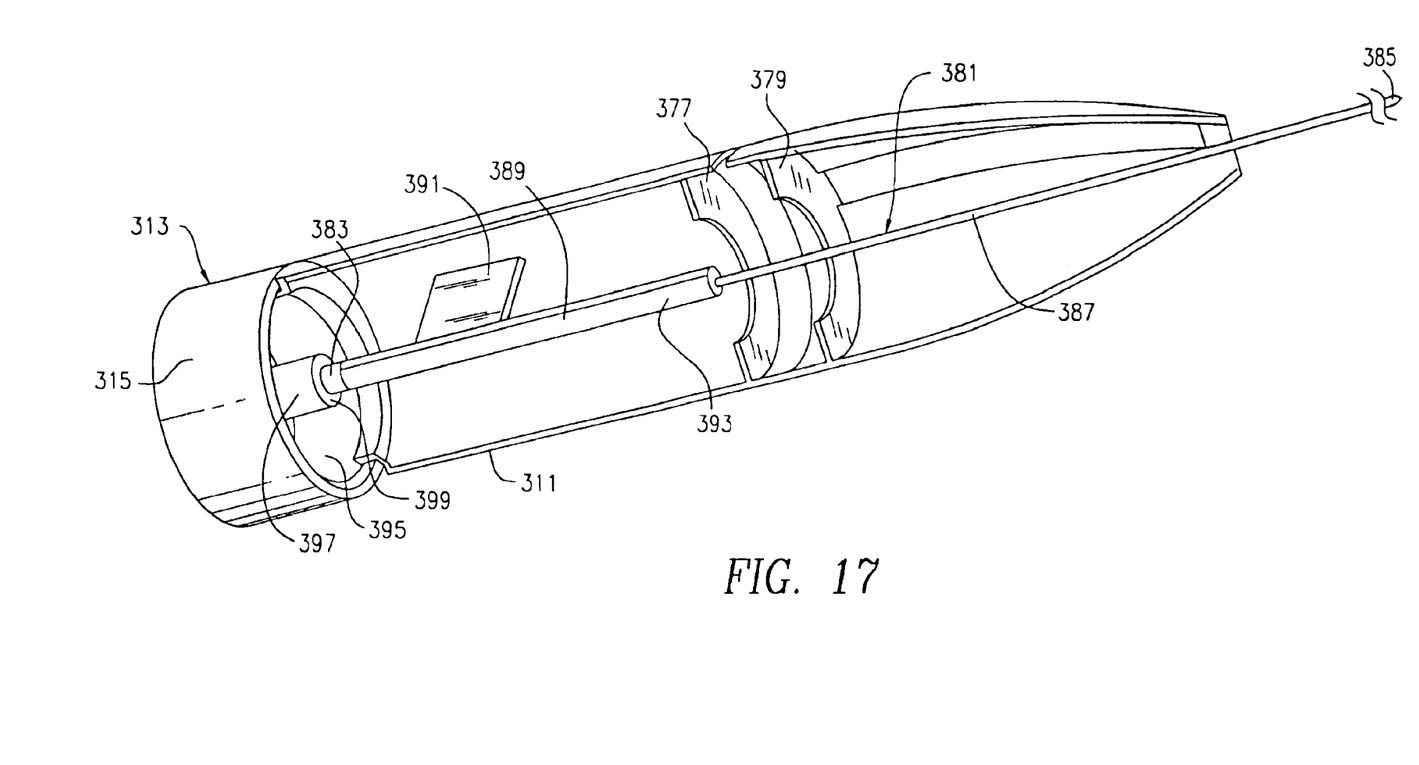
FIG. 17 is a partial cross-sectional view of the RF device shown in FIG. 14, showing an inner camming rod.

Referring now to FIG. 17, the RF device 310 includes an inner camming rod 381 that has a proximal end 383 which is threadly attached by a screw or other fastener to the finger knob 313 and a distal tapered end 385 either attached to or adjacent to the jaws 325, 327 (see FIG. 14). The inner camming rod 381 has a distal portion 387 that is sized and shaped to be coaxially received within the inner tube 321, and a proximal portion 389 that includes a rotation-limiting protrusion 391 attached thereto. The rotation-limiting protrusion 391 is utilized to prevent the inner camming rod 381 from rotating. An outer tube 393 surrounds the proximal portion 389 of the inner camming rod 381. The finger knob 313 includes a cylindrical portion 395 and a center portion 397 defined by a lumen 399 sized and shaped to receive the proximal end 383 of the inner camming rod 381. The inner camming rod 381 is axially movable between a retracted position when the finger knob 313 is rotated in one direction (e.g., clockwise), in which the inner camming rod 381 moves toward the finger knob 313 such that the jaws 325, 327 move to their closed configuration (see FIG. 19), and an extended position when the finger knob 313 is rotated in an opposite direction (e.g., counterclockwise), in which the distal tapered end 385 of the inner camming rod 381 moves toward the jaws and contacts the jaws 325, 327 at their abutting center end 401 (see FIG. 19) such that the jaws 325, 327 move to their open configuration (see FIG. 20). The amount of rotation of the finger knob 313 determines the extent that the jaws 325, 327 open. After surgery is performed, the inner camming rod 381 may be retracted in a direction toward the finger knob 313 so as to allow the jaws 325, 327 to move to their closed configuration as they pass through narrow sections of the uterus and the cervix.

In operation, prior to inserting the RF device 310 into the uterine cavity 114', the uterine sound is used to measure depth between the fundus 120' and the cervix 104'. More particularly, a sound (not shown) is inserted into the vaginal orifice (not shown) and guided through the cervical canal 106', and into the uterine cavity 114' until the sound is in contact with the fundus 120'. The RF device 310 is then inserted transcervically into the vaginal orifice (not shown) and guided to the cervix 104'. Note that in the foregoing step, the outer sheath 319 is in its fully extended configuration as shown in FIG. 18.

The RF device 310 is then guided through the cervical canal 106', and into the uterine cavity 114' until the linkage assembly 323 is adjacent to the fundus 120' of the uterine cavity 114'. Next, the outer sheath 319 moves, via manual manipulation of the extension 353 in the manner described previously, into its fully retracted configuration as shown in FIG. 19, so as to expose the linkage assembly 323.

After the linkage assembly 323 is exposed, the finger knob 313 is rotated such that the jaws 325, 327 assume their open configuration as shown in FIG. 20. RF energy is supplied to one or more of the electrode legs 331, 333, and the arm 335 of the effector strip 329 such that RF energy is emitted therefrom to the tissues surrounding and between the electrode legs 331, 333 and the arm 335 for a predetermined time interval. The emitted RF energy heats and ablates these tissue areas. Then, the polarity of the electrode legs 331, 333, and the arm 335 is altered to produce the desired polarization configuration. RF energy is then re-supplied to one or more of the electrode legs 331, 333, and the arm 335. During operation, the RF device 310 can be moved, for example back and forth or tilted, such that the effector strip 329 is also moved within the uterine cavity 114' of the patient. Also, during operation, the tension of the effector strip 329 can be adjusted, via manual manipulation of the protrusion 359, in the manner described previously. Then, the jaws 325, 327 assume their closed configuration and the outer sheath 319 is moved to its extended position. Lastly, the RF device 310 is removed from the uterine cavity 114', the cervical canal 110', and the vaginal orifice (not shown). Because the electrode legs 331, 333, and the arm 335 can be connected in various arrangements and can switch electrical connections at various time intervals, increased thermal coverage is achieved.

It can be appreciated that the present invention provides numerous advantages. For instance, the present invention enables the use of thermal ablation therapy for treating menorrhagia in women, even if they have benign uterine pathology, without employing a balloon in the uterine cavity 110 (see FIG. 7). The RF device 10, 210, and 310 can treat menorrhagia without requiring surgery and can be used in a physician's office. The RF device 10, 210, and 310 can penetrate deeply into the uterine cavity 110 such that a high amenorrhea rate (no bleeding) is achieved.

It should be noted that the RF device 10, 210, and 310 can have numerous modifications and variations. For instance, the RF device 10, 210, and 310 can be either non-disposable or disposable. The RF device 10, 210, and 310 can be either bipolar as described previously, monopolar with a return or ground electrode placed on the body, or sesquipolar. Although a pair of RF applicators 30, 32 of the RF electrode 10 is shown, the number of RF applicators 30, 32 can vary. Likewise, although a pair of spring wire electrodes 213, 215 is shown, the number of spring wire electrodes 213, 215 can vary. In one aspect, the RF applicators 30, 32 are formed as a single piece (not shown), which may be suitable for delivering RF energy in monopolar fashion. Additional electrode legs can be employed within the RF device 10. In one aspect, a third electrode leg (not shown) is provided between the electrode legs 34, 36. The electrode legs 34, 36 can be segmented so as to regulate the amount of RF energy emitted from the RF device 10. The RF devices 10, 210, and 310 can be operated in water, dextrose, or sorbitol as non-conductive and non-ionic solutions. Further, the RF device 10, 210 can include flexible members (not shown) to improve conformity to the uterine cavity 110. In one aspect, the tube 211 of the RF device 210 is stationary and the spring wire electrodes 213, 215 move relative to the tube 211 by using an actuating mechanism (not shown). The first and second links 38, 68 of the RF device 10 and the central links 221, 251 of the RF device 210 may be conductive or non-conductive. Although a pair of jaws 325, 327 of the RF device 310 is shown, the number of jaws 325, 327 can vary. The effector strip 329 can be segmented so as to regulate the amount of RF energy emitted from the RF device 310. In one aspect, a breakaway bearing (not shown) can be employed to prevent excessive spreading of the jaws 325, 327 within a smaller uterus. The jaws 325, 327 can also be moved to their closed configuration by adjusting the tension of the effector strip 329. Further, the electrode legs 331, 333 and the arm 335 can have temperature sensors (e.g., thermocouples, thermistors, fiber optic) on their surfaces such that the temperature is monitored and controlled by using temperature feedback. All such variations and modifications are intended to be included within the scope of the invention as defined in the appended claims.

What is claimed is:

1. An electrode instrument used for thermal ablation therapy in an uterus of a patient, comprising an outer sheath, an electrode head connected to said outer sheath and having at least a first and second electrode for emitting RF energy, said first electrode having a proximal end connected to said outer sheath and a distal end positioned remote from said proximal end of said first electrode, said second electrode having a proximal end connected to said outer sheath and a distal end positioned remote from said proximal end of said second electrode, said first and second electrodes being movable between a collapsed configuration, in which said distal ends of said first and second electrodes are positioned proximate to each other and remote from opposed sidewalls of the patient's uterus, and a deployed configuration, in which said distal ends of said first and second electrodes are positioned remote from each other such that said distal end of said first electrode is positioned adjacent to one sidewall of the patient's uterus and said distal end of said second electrode is positioned adjacent to an opposite sidewall of the patient's uterus, and a first linkage mechanism connected between said first and second electrodes for maintaining said first and second electrodes in their deployed configuration, at least one portion of said first linkage mechanism being electrically connected to said first electrode and forming a part of said first electrode, said first linkage mechanism being positioned adjacent to a top wall of the patient's uterus when said first and second electrodes are in their said deployed configuration, wherein said first linkage mechanism cooperates with said first and second electrodes when said first and second electrodes are in their said deployed configuration so as to approximate the shape of the patient's uterus.

2. The electrode instrument of claim 1, further comprising an actuator rod connected to said first linkage mechanism, said actuator rod cooperating with said first linkage mechanism to move said first and second, electrodes between their collapsed and deployed configurations.

3. The electrode instrument of claim 2, wherein said first linkage mechanism is movable between a first position, in which said first linkage mechanism is substantially parallel to said first and second electrodes when said first and second electrodes are in their collapsed configuration, and a second position, in which said linkage mechanism is at an acute angle relative to said first and second electrodes when said first and second electrodes are in their deployed configuration.

4. The electrode instrument of claim 3, wherein said first linkage mechanism includes a first arm electrically connected to said first electrode and a second arm connected to said first arm, said second arm being electrically connected to said second electrode.

5. The electrode instrument of claim 4, wherein said electrode head assumes a substantially cylindrical shape when said first and second electrodes are in their said collapsed configuration, and wherein said electrode head assumes a substantially triangular shape when said first and second electrodes are in their said deployed configuration.

6. The electrode instrument of claim 5, wherein one of said first and second electrodes is an active electrode and the other of said first and second electrodes is a return electrode.

7. The electrode instrument of claim 6, wherein said electrode head further includes a third and fourth electrode for emitting RF energy, said third and fourth electrodes being movable between a collapsed configuration, in which said third and fourth electrodes are proximate to each other, and a deployed configuration, in which said third and fourth electrodes are remote from each other, and a second linkage mechanism connected between said third and fourth electrodes, for maintaining said third and fourth electrodes in their deployed configuration.

8. The electrode instrument of claim 7, wherein amid third electrode is positioned adjacent said first electrode and said fourth electrode is positioned adjacent to said second electrode.

9. The electrode instrument of claim 8, wherein the polarity of said first, second, third, and fourth electrodes can be selectively varied.

10. The electrode instrument of claim 9, wherein one of said first, second, third, and fourth electrodes can be an active electrode for a first predetermined time period and can be a return electrode for a second predetermined time period.

11. The electrode instrument of claim 10, wherein said first and third electrodes emit RF energy between each other, and said second and fourth electrodes emit RF energy between each other.

12. The electrode instrument of claim 11, wherein said first and second electrodes emit RF energy between each other, and said third and fourth electrodes emit RF energy between each other.

13. The electrode instrument of claim 12, wherein said first, second, third, and fourth electrodes are sized and shaped to emit bipolar RF energy.

14. The electrode instrument of claim 1, wherein said first and second electrodes are sized and shaped to emit monopolar RF energy.

15. The electrode instrument of claim 1, wherein said electrode head further includes a tube sized and shaped so as to receive said first and second electrodes when said first and second electrodes are in their said collapsed configuration.

16. The electrode instrument of claim 15, wherein said first and second electrodes have spring memory characteristics.

17. The electrode instrument of claim 16, wherein said tube is moveable between a distal position, in which said first and second electrodes are substantially compressed within said tube, and a proximal position, in which said first and second electrodes are extended from said tube.

18. The electrode instrument of claim 17, wherein said first and second electrodes have a predetermined shape set therein.

19. The electrode instrument of claim 18, wherein said first and second electrodes assume a substantially triangular shape when said tube is in its said proximal position.

20. The electrode instrument of claim 1, wherein said linkage mechanism includes a pair of jaws sized and shaped to move said first and second electrodes between their said collapsed and deployed configurations.

21. The electrode instrument of claim 20, wherein said electrode head further includes a sheath sized and shaped so as to receive said first and second electrodes when said first and second electrodes are in their said collapsed configuration.

22. The electrode instrument of claim 21, wherein said electrode head further includes an arm having one end connected to said first electrode and an opposite end connected to said second electrode.

23. The electrode instrument of claim 22, wherein the polarity of said first electrode, said second electrode, and said arm can be selectively varied.

24. The electrode instrument of claim 23, wherein one of said first electrode, said second electrode, and said arm can be an active electrode for a first predetermined time period and can be a return electrode for a second predetermined time period.

25. The electrode instrument of claim 24, wherein the tension of said first electrode, said second electrode, and said arm can be varied.

26. The electrode instrument of claim 1, wherein said first linkage mechanism has a length and is positioned between said first and second electrodes in a substantially linear fashion along the entire length of said first linkage mechanism when said first and second electrodes are in their said deployed configuration.

27. An electrode instrument used for thermal ablation therapy in an uterus of a patient, comprising an outer sheath, an electrode head connected to said outer sheath and having at least a first and second electrode for emitting RF energy, said first electrode having a proximal end connected to said outer sheath and a distal end positioned remote from said proximal end of said first electrode, said second electrode having a proximal end connected to said outer sheath and a distal end positioned remote from said proximal end of said second electrode, said first and second electrodes being movable between a collapsed configuration, in which said distal ends of said first and second electrodes are positioned proximate to each other and remote from opposed sidewalls of the patient's uterus, and a deployed configuration, in which said distal ends of said first and second electrodes are positioned remote from each other such that said distal end of said first electrode is positioned adjacent to one sidewall of the patient's uterus and said distal end of said second electrode is positioned adjacent to an opposite sidewall of the patient's uterus, a first linkage mechanism connected between said first and second electrodes, and an actuator rod connected to said linkage mechanism so as to cooperate with said linkage mechanism to move said first and second electrodes between their collapsed and deployed configurations, at least one portion of said first linkage mechanism being electrically connected to said first electrode and forming a part of said first electrode, said first linkage mechanism being positioned adjacent to a top wall of the patient's uterus when said first and second electrodes are in their said developed configuration, wherein said first linkage mechanism cooperates with said first and second electrodes when said first and second electrodes are in their said deployed configuration so as to approximate the shape of the patient's uterus.

* * * * *